(12) United States Patent
Ito et al.

(10) Patent No.: US 6,476,179 B1
(45) Date of Patent: Nov. 5, 2002

(54) PROCESS FOR PRODUCING RAW POLYCARBONATE RESIN MATERIAL AND PRODUCING POLYCARBONATE RESIN

(75) Inventors: Hajime Ito, Tokuyama (JP); Akio Suwa, Ichihara (JP); Jun Kohiruimaki, Ichihara (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/926,501

(22) PCT Filed: Mar. 2, 2001

(86) PCT No.: PCT/JP01/01638

§ 371 (c)(1), (2), (4) Date: Nov. 13, 2001

(87) PCT Pub. No.: WO01/66616

PCT Pub. Date: Sep. 13, 2001

(30) Foreign Application Priority Data

Mar. 10, 2000 (JP) .......................................... 2000-065872
Jul. 27, 2000 (JP) .......................................... 2000-226962
Dec. 5, 2000 (JP) .......................................... 2000-369725

(51) Int. Cl.$^7$ ................................................ C08G 64/00
(52) U.S. Cl. ................................................ 528/196; 528/198
(58) Field of Search .................................. 528/196, 198

(56) References Cited

FOREIGN PATENT DOCUMENTS

JP              9-208685              8/1987

*Primary Examiner*—Terressa M. Boykin
(74) *Attorney, Agent, or Firm*—Oblon, Spivak, McClelland, Maier & Neustadt, P.C.

(57) ABSTRACT

The invention relates to an inexpensive and simple method for producing a starting material for polycarbonate resin and for producing polycarbonate resin. In the method for producing a starting material for polycarbonate resin production through interfacial polymerization, (I) a molten bisphenol compound is mixed and dissolved in an aqueous alkali solution at 20 to 80° C., or (II) it is, without being solidified, directly mixed with water to be in liquid at a temperature not higher than the melting point of the bisphenol compound, and then dissolved in an aqueous alkali solution.

17 Claims, No Drawings

PROCESS FOR PRODUCING RAW POLYCARBONATE RESIN MATERIAL AND PRODUCING POLYCARBONATE RESIN

TECHNICAL FIELD

The present invention relates to a method for producing a starting material for polycarbonate resin and to a method for producing polycarbonate resin. More precisely, the invention relates to an inexpensive and simple method for producing a starting material for polycarbonate resin and for producing polycarbonate resin.

BACKGROUND ART

Polycarbonate resin is a type of engineering plastics having well-balanced transparency, heat resistance and mechanical strength, and is used in many fields. Based on its overall characteristics of transparency, heat resistance, hydrolysis resistance and dimensional stability, polycarbonate resin is especially much used these days for raw materials for optical recording media such as compact discs, laser discs, optical memory cards, optical discs, digital video discs, etc. Polycarbonate resin of high transparency suitable to optical appliances including such optical recording media is produced through interfacial polymerization.

For producing polycarbonate resin through interfacial polymerization, generally employed is a method of reacting a bisphenol compound with phosgene. in the presence of an organic solvent and an aqueous alkali solution. For this, it is well known that a granulated solid bisphenol compound, which serves as the essential starting material for polycarbonate resin, is dissolved in an aqueous alkali solution and phosgene gas is introduced into the resulting solution.

The bisphenol compound, which is the essential starting material for polycarbonate resin, is granulated in a complicated process. For example, 2,2-bis(4-hydroxyphenyl)propane is, after produced through reaction of phenol with acetone, purified in many steps and then granulated in the final step. For granulating the bisphenol compound, used is a granulator such as a spray drier or the like, in which the bisphenol compound is formed into liquid drops and then cooled and solidified.

For producing polycarbonate resin from the bisphenol compound through interfacial polymerization, solid grains of the bisphenol compound having been solidified and granulated in the process as above are dissolved in an aqueous alkali solution, and the resulting solution is used in polycondensation.

The process for producing the bisphenol compound that serves as a starting material in producing polycarbonate resin through interfacial polymerization, and the process for producing polycarbonate resin require complicated many steps as in the above, and are therefore problematic in that many plants and much labor are needed and the production costs are high.

The present invention is to provide an inexpensive and simple method for producing a starting material for polycarbonate resin and for producing polycarbonate resin.

DISCLOSURE OF THE INVENTION

We, the present inventors have assiduously studied to solve the problems noted above, and, as a result, have found that, in a process for producing polycarbonate resin through interfacial polymerization, (I) when a bisphenol compound prepared in melt in a process of bisphenol compound production is, without being granulated, directly mixed in an aqueous alkali solution while it is in melt, and when the thus-prepared aqueous alkali solution of the bisphenol compound is used as the starting material for polycarbonate resin production, or (II) when a bisphenol compound prepared in melt in a process of bisphenol compound production is, without being solidified, directly mixed with water to be in liquid at a temperature not higher than the melting point of the bisphenol compound, and then dissolved in an aqueous alkali solution, and when the thus-prepared aqueous alkali solution of the bisphenol compound is used as the starting material for polycarbonate resin production through interfacial polymerization, then the above-mentioned object can be attained. On the basis of these findings, we have completed the present invention (including first and second aspects).

Specifically, the invention is summarized as follows:

I. First Aspect of the Invention
  (1) A method for producing a starting material for polycarbonate resin production through interfacial polymerization, which is characterized in that a bisphenol compound prepared in melt in a process of bisphenol compound production is mixed and dissolved in an aqueous alkali solution at 20 to 80° C.
  (2) The method for producing a starting material for polycarbonate resin of above (1), wherein the bisphenol compound includes bis(4-hydroxyphenyl)alkanes.
  (3) A method for producing polycarbonate resin, which is characterized in that a bisphenol compound prepared in melt in a process of bisphenol compound production is mixed and dissolved in an aqueous alkali solution at 20 to 80° C, and the resulting aqueous alkali solution of the bisphenol compound is used as the starting material for polycarbonate resin production through interfacial polymerization.

II. Second Aspect of the Invention
  (1) A method for producing a starting material for polycarbonate resin, which is characterized in that a bisphenol compound prepared in melt in a process of bisphenol compound production is, without being solidified, directly mixed with water to be in liquid at a temperature not higher than the melting point of the bisphenol compound, and then dissolved in an aqueous alkali solution.
  (2) The method for producing a starting material for polycarbonate resin of above (1), wherein the bisphenol compound includes bis(4-hydroxyphenyl)alkanes.
  (3) A method for producing polycarbonate resin, which is characterized in that a bisphenol compound prepared in melt in a process of bisphenol compound production is, without being solidified, directly mixed with water to be in liquid at a temperature not higher than the melting point of the bisphenol compound, and then dissolved in an aqueous alkali solution, and the resulting aqueous alkali solution of the bisphenol compound is used as the starting material for polycarbonate resin production through interfacial polymerization.

BEST MODE OF THE CARRYING OUT THE INVENTION

Modes of carrying out the invention are described hereinunder.

I. First Aspect of the Invention

In this section, the first aspect of the invention will be simply referred to as the invention.

In the method of the invention for producing a starting material for polycarbonate resin production through interfacial polymerization, a bisphenol compound prepared in melt in a process of bisphenol compound production is mixed and dissolved in an aqueous alkali solution at 20 to 80°C; and, in the method of the invention for producing polycarbonate resin, the resulting aqueous alkali solution of the bisphenol compound is used as the starting material for polycarbonate resin production.

In the method of the invention, the step of polycarbonate resin production through interfacial polymerization is per-se known. It comprises adding phosgene to the aqueous alkali solution of a bisphenol compound, with stirring it in the presence of an organic solvent such as methylene chloride or the like capable of well dissolving polycarbonate resin, to thereby form a polycarbonate oligomer having a chloroformate terminal, followed by further polymerizing the oligomer.

The bisphenol compound that serves as the essential starting material in the polycarbonate resin production includes, for example, 4,4'-dihydroxybiphenyls such as 4,4'-dihydroxybiphenyl, 3,3'-difluoro-4,4'-dihydroxybiphenyl, 4,4'-dihydroxy-3,3'-dimethyldiphenyl, 4,4'-dihydroxy-2,2'-dimethylbiphenyl, 4,4'-dihydroxy-3,3'-dicyclohexylbiphenyl, etc.; bis(4-hydroxyphenyl)methanes such as bis(4-hydroxyphenyl)methane, bis(4-hydroxyphenyl)diphenylmethane, bis(4-hydroxyphenyl)phenylmethane, bis(3-methyl-4-hydroxyphenyl)methane, bis(3-nonyl-4-hydroxyphenyl)methane, bis(3,5-dimethyl-4-hydroxyphenyl)methane, bis(3,5-dibromo-4-hydroxyphenyl)methane, bis(3-chloro-4-hydroxyphenyl)methane, bis(3-fluoro-4-hydroxyphenyl)methane, bis(2-tert-butyl-4-hydroxyphenyl)phenylmethane,; bis(2-hydroxyphenyl)methanes such as bis(2-hydroxyphenyl)methane, 2-hydroxyphenyl-4-hydroxyphenylmethane, bis(2-hydroxy-4-methylphenyl)methane, bis(2-hydroxy-4-methyl-6-tert-butylphenyl)methane, bis(2-hydroxy-4,6-dimethylphenyl)methane, etc.; bis(4-hydroxyphenyl)ethanes such as 1,1-bis(4-hydroxyphenyl)ethane, 1,2-bis(4-hydroxyphenyl)ethane, 1,1-bis(4-hydroxyphenyl-1-phenylethane, 1,1-bis(4-hydroxy-3-methylphenyl)-1-phenylethane, 1,1-bis(4-hydroxy-3-methylphenyl)-1-phenylethane, 2-(4-hydroxy-3-methylphenyl)-2-(4-hydroxyphenyl)-1-phenylethane, 1,1-bis(2-tert-butyl-4-hydroxy-3-methylphenyl)ethane, 1-phenyl-1,1-bis(3-fluoro-4-hydroxyphenyl)ethane,; bis(2-hydroxyphenyl)ethanes such as 1,1-bis(2-hydroxy-4-methylphenyl)ethane, etc.; bis(4-hydroxyphenyl)propanes such as 2,2-bis(4-hydroxyphenyl)propane, 1,1-bis(4-hydroxyphenyl)propane, 2,2-bis(2-methyl-4-hydroxyphenyl)propane, 2,2-bis(3-methyl4-hydroxyphenyl)propane, 2,2-bis(3-isopropyl-4-hydroxyphenyl)propane, 2,2-bis(3-sec-butyl-4-hydroxyphenyl)propane, 2,2-bis(3-phenyl-4-hydroxyphenyl)propane, 2,2-bis(3-cyclohexyl-4-hydroxyphenyl)propane, 2,2-bis(3-chloro-4-hydroxyphenyl)propane, 2,2-bis(3-fluoro-4-hydroxyphenyl)propane, 2,2-bis(3-bromo-4-hydroxyphenyl)propane, 2,2-bis(4-hydroxy-3,5-dimethylphenyl)propane, 1,1-bis(2-tert-butyl-4-hydroxy-5-methylphenyl)propane, 2,2-bis(4-hydroxy-3,5-dichlorophenyl)propane, 2,2-bis(4-hydroxy-3,5-difluorophenyl)propane, 2,2-bis(4-hydroxy-3,5-bromophenyl)propane, 2,2-bis(3-bromo-4-hydroxy-5-chlorophenyl)propane, 2,2-bis(4-hydroxyphenyl)-1,1,1,3,3,3-hexafluoropropane,; bis(2-hydroxyphenyl)propanes such as 2,2-bis(2-hydroxy-4-sec-butylphenyl)propane, 2,2-bis(2-hydroxy-4,6-dimethylphenyl)propane, etc.; bis(4-hydroxyphenyl)butanes such as 2,2-bis (4-hydroxyphenyl)butane, 2,2-(3-methyl-4-hydroxyphenyl)butane, 1,1-bis(4-hydroxyphenyl)-2-methylpropane, 1,1-bis(2-tert-butyl-4-hydroxy-5-methylphenyl)-2-methylpropane, 1,1-bis(2-butyl-4-hydroxy-5-methylphenyl)butane, 1,1-bis(2-tert-butyl-4-hydroxy-5-methylphenyl)butane, 1,1-bis(2-methyl-4-hydroxy5-tert-pentylphenyl)butane, 2,2-bis(4-hydroxy-3,5-dichlorophenyl)butane, 2,2-bis(4-hydroxy-3,5-dibromophenyl)butane, 2,2-bis(4-hydroxyphenyl)-3-methylbutane, 1,1-bis (4-hydroxyphenyl)-3-methylbutane, etc.; bis(hydroxyphenyl)alkanes such as 3,3-bis(4-hydroxyphenyl)pentane, 2,2-bis(4-hydroxyphenyl)hexane, 2,2,-bis(4-hydroxyphenyl)heptane, 2,2-bis(2-tert-butyl-4-hydroxy-5-methylphenyl)heptane, 2,2-bis(4-hydroxyphenyl)octane, 2,2-bis(4-hydroxyphenyl)nonane, 2,2-bis(4-hydroxyphenyl)decane, 1,1-bis(4-hydroxyphenyl)cyclopentane, 1,1-bis(4-hydroxyphenyl)cyclohexane, 1,1-bis(3-methyl-4-hydroxyphenyl)cyclohexane, 1,1-bis(4-hydroxy-3,5-dimethylphenyl)cyclohexane, 1,1-bis(3-cyclohexyl-4-hydroxyphenyl)cyclohexane, 1,1-bis(3-phenyl-4-hydroxyphenyl)cyclohexane, 1,1-bis(4-hydroxyphenyl)-3,3,5-trimethylcyclohexane, 1,1-bis(3-methyl-4-hydroxyphenyl)-3,3,5-trimethylcyclohexane, etc.; bis(4-hydroxyphenyl)ethers such as bis(4-hydroxyphenyl)ether, bis(3-fluoro-4-hydroxyphenyl)ether, etc.; bis(4-hydroxyphenyl)sulfides such as bis(4-hydroxyphenyl)sulfide, bis(3-methyl-4-hydroxyphenyl)sulfide, etc.; bis (4-hydroxyphenyl)sulfoxides such as bis(4-hydroxyphenyl)sulfoxide, bis(3-methyl-4-hydroxyphenyl)sulfoxide, etc.; bis (4-hydroxyphenyl)sulfones such as bis(4-hydroxyphenyl)sulfone, bis(3-methyl-4-hydroxyphenyl)sulfone, bis(3-phenyl-4-hydroxyphenyl)sulfone, etc.; bis(4-hydroxyphenyl)ketones such as 4,4'-dihydroxybenzophenone, etc.; bis(hydroxyphenyl)fluorenes such as 9,9-bis(4-hydroxyphenyl)fluorene, 9,9-bis(3-methyl4-hydroxyphenyl)fluorene, 9,9-bis(3-phenyl-4-hydroxyphenyl)fluorene, etc.; dihydroxy-p-terphenyls such as 4,4'-dihydroxy-p-terphenyl, etc.; bis(hydroxyphenyl)pyrazines such as 2,5-bis(4-hydroxyphenyl)pyrazine, 2,5-bis(4-hydroxyphenyl)-3,6-dimethylpyrazine, 2,5-bis(4-hydroxyphenyl)-2,6-diethylpyrazine, etc.; bis (hydroxyphenyl)menthanes such as 1,8-bis(4-hydroxyphenyl)menthane, 2,8-bis(4-hydroxyphenyl)menthane, 1,8-bis(3-methyl-4-hydroxyphenyl)menthane, 1,8-bis(4-hydroxy-3,5-dimethylphenyl)menthane,etc.; bis[2-(4-hydroxyphenyl)-2-propyl]benzenes such as 1,4-bis[2-(4-hydroxyphenyl)-2-propyl]benzene, 1,3-bis[2-(4-hydroxyphenyl)-2-propyl]benzene, etc.; dihydroxynaphthalenes such as 1,3-dihydroxynaphthalene, 1,4-dihydroxynaphthalene, 1,5-dihydroxynaphthalene, 2,6-dihydroxynaphthalene, 2,7-dihydroxynaphthalene, etc.; dihydroxybenzenes such as resorcinol, hydroquinone, catechol, etc.

Of those bisphenols, especially preferred are bis(4-hydroxyphenyl)alkanes, as the polycarbonate resins having started from them have well balanced physical properties of transparency, heat resistance, hydrolysis resistance and dimensional stability, and are favorable to materials for optical appliances.

Regarding the production of the bisphenols, for example, 2,2-bis(4-hydroxyphenyl)propane is produced by reacting acetone with phenol in the presence of a catalyst. For the catalyst, for example, preferred are sulfonic acid-type cation-exchange resins such as sulfonated styrene-divinylbenzene copolymers, sulfonated crosslinked styrene polymers, phenol-formaldehyde-sulfonic acid resins, benzene-formaldehyde-sulfonic acid resins, etc. In the case, preferably used are alkylmercaptans serving as a catalyst promoter. Excess phenol over acetone is reacted with acetone.

The reaction mixture contains non-reacted phenol and acetone, the catalyst used and also side products such as water, alkylmercaptans, organic-sulfur compounds and coloring matters, in addition to the intended product, 2,2-bis (4hydroxyphenyl)propane. Therefore, the reaction mixture is subjected to distillation under reduced pressure to remove the non-reacted acetone, water and alkylmercaptans. Then, this is further subjected to distillation under reduced pressure to remove the non-reacted phenol, in the next step of concentrating the product, 2,2-bis(4-hydroxyphenyl) propane.

The concentrate residue obtained in the concentration step has a 2,2-bis(4-hydroxyphenyl)propane concentration of from 20 to 50% by weight, preferably from 20 to 40% by weight, and this is then cooled to 40 to 70° C. in the next crystallization step, in which an adduct of 2,2-bis (4-hydroxyphenyl)propane and phenol (hereinafter referred to as a phenol adduct) is crystallized out in slurry. The concentrate residue slurry is then filtered or centrifuged whereby the phenol adduct crystal is separated from the mother liquid. The thus-obtained crystal, 2,2-bis(4-hydroxyphenyl)propane/phenol 1/1 adduct is heated and melted at 100 to 160° C., and the resulting melt mixture is subjected to distillation under reduced pressure to remove phenol. Thus is obtained 2,2-bis(4-hydroxyphenyl)propane.

2,2-Bis(4-hydroxyphenyl)propane thus obtained is in melt. In general, this is formed into liquid drops, and then cooled and solidified into a granular product, in a granulator such as a spray drier or the like. Then, the resulting granular solid of 2,2-bis(4-hydroxyphenyl)propane is transported into an apparatus for polycarbonate resin production, in which this is dissolved in an aqueous alkali solution such as an aqueous sodium hydroxide solution or the like in the unit for preparing the starting material for polycarbonate resin, and the resulting solution is used for polycarbonate resin production.

In the present invention, the molten bisphenol such as 2,2-bis(4-hydroxyphenyl)propane prepared in the process as above is, without being solidified and granulated in the granulation step, directly dissolved in an aqueous alkali solution such as an aqueous sodium hydroxide solution or the like in the step of preparing the starting material for polycarbonate resin production. The invention is characterized by the direct preparation of the starting material for polycarbonate resin production. In the invention, the temperature of the aqueous alkali solution in which the bisphenol is dissolved is controlled to fall between 20 and 80° C. If the temperature of the aqueous alkali solution is lower than 20° C., a lot of time will be taken to dissolve the bisphenol in the solution, and the productivity of polycarbonate resin will be low. On the other hand, if the temperature is higher than 80° C., the bisphenol will be thermally decomposed and discolored, and, in addition, the aqueous alkali solution will corrode the apparatus.

For mixing the molten bisphenol with such an aqueous alkali solution, for example, employed is a dissolution tank equipped with a line mixer or a stirrer. Preferably, the atmosphere in the apparatus is previously purged with an inert gas such as nitrogen gas or the like so that the mixing operation can be effected in such an inert gas atmosphere. The temperature of the molten bisphenol is not lower than the melting point of the bisphenol, but is preferably higher by at most 80° C. than the melting point thereof. If the temperature of the bisphenol melt is higher than it, the bisphenol will be decomposed and discolored.

For the aqueous alkali solution in which the molten bisphenol is dissolved, preferred is sodium hydroxide. In place of sodium hydroxide, however, any other alkali metal hydroxides and alkaline earth metal hydroxides may also be employed. The concentration of the aqueous alkali solution may fall between 2 and 47% by weight. Preferably, the amount of the aqueous alkali solution to be used falls between 1.9 and 2.5 mols relative to one mol of the bisphenol to be dissolved in the solution. Regarding the reaction between bisphenol and alkali such as sodium hydroxide, one mol of bisphenol theoretically reacts with 2 mols of sodium hydroxide. In practical reaction, however, it is desirable that the amount of sodium hydroxide is excessive in some degree over bisphenol.

When the molten bisphenol is mixed with such an aqueous alkali solution, a reducing agent is preferably added thereto. The reducing agent may be any ordinary one. For example, preferred are sodium sulfite, sodium thiosulfate, sodium dithionite (hydrosulfite), etc. Its amount may fall between 10 and 1,000 ppm by weight of the aqueous alkali solution. The reducing agent may be added to the aqueous alkali solution before bisphenol is added to the solution, or may be added to water which is used for controlling the alkali concentration of the solution, or may be added to the aqueous alkali solution simultaneously with molten bisphenol added thereto. The reducing agent added improves the color tone of the polycarbonate resin that starts from the aqueous alkali solution of bisphenol obtained herein.

The method of the invention for producing polycarbonate that starts from the aqueous alkali solution of bisphenol compound prepared in the manner as above may be the same as that for conventional polycarbonate resin production through interfacial polymerization, except that it does not require the step of dissolving solid grains of bisphenol compound in an aqueous alkaline solution.

For example, phosgene is added to the aqueous alkali solution of bisphenol compound, with stirring it in the presence of an organic solvent such as methylene chloride or the like capable of well dissolving polycarbonate resin, to thereby form a polycarbonate oligomer having a chloroformate terminal, and the oligomer is further polymerized. The polycondensation condition, the catalyst, the mode of molecular weight control and the additives to be optionally added for the method may be the same as those for conventional methods.

The invention is described more concretely with reference to the following Examples and Comparative Examples.

EXAMPLE I-1

A 300-ml reactor equipped with a condenser and a stirrer was purged with nitrogen gas. 224 g of an aqueous sodium hydroxide solution having a concentration of 5.6% by weight, and 0.035 g of hydrosulfite serving as a reducing agent were put into the reactor, and heated up to 50° C.

Next, with stirring the mixture in the reactor at 350 rpm, 35 g of a melt (at 170° C.) of 2,2-bis(4-hydroxyphenyl) propane was poured into it. Having been poured thereinto, the melt of 2,2-bis(4-hydroxyphenyl)propane immediately dissolved in the aqueous sodium hydroxide solution, without forming deposit.

The APHA color hue of the aqueous sodium hydroxide solution of 2,2-bis (4-hydroxyphenyl)propane was at most 10, and did not differ from that of the solution prepared by dissolving granulated solid 2,2-bis(4-hydroxyphenyl) propane in aqueous sodium hydroxide.

EXAMPLE I-2

A 300-ml reactor equipped with a condenser and a stirrer was purged with nitrogen gas. Bubbled with nitrogen gas, 224 g of an aqueous sodium hydroxide solution having a concentration of 5.6% by weight was put into the reactor, and heated up to 50° C.

Next, with stirring the mixture in the reactor at 350 rpm, 35 g of a melt (at 170° C.) of 2,2-bis(4-hydroxyphenyl) propane and 0.035 g of solid hydrosulfite serving as a reducing agent were fed into the reactor through different feed lines. Having been thus fed thereinto, the melt of 2,2-bis(4-hydroxyphenyl)propane immediately dissolved in the aqueous sodium hydroxide solution, without forming deposit.

The APHA color hue of the aqueous sodium hydroxide solution of 2,2-bis (4-hydroxyphenyl)propane was at most 10, and did not differ from that of the solution prepared by dissolving granulated solid 2,2-bis(4-hydroxyphenyl) propane in aqueous sodium hydroxide.

EXAMPLE I-3

A 300-ml reactor equipped with a condenser and a stirrer was purged with nitrogen gas. 224 g of an aqueous sodium hydroxide solution having a concentration of 5.6% by weight, 0.035 g of hydrosulfite serving as a reducing agent, and 28 g of solid granular 2,2-bis(4-hydroxyphenyl)propane were put into the reactor, and heated up to 40° C.

Next, with stirring the mixture in the reactor at 350 rpm, 7 g of a melt (at 170° C.) of 2,2-bis(4-hydroxyphenyl) propane was poured into it. Having been poured thereinto, the melt of 2,2-bis (4-hydroxyphenyl)propane partly deposited, but, after 6 minutes, it completely dissolved in the aqueous sodium hydroxide solution.

The APHA color hue of the aqueous sodium hydroxide solution of 2,2-bis (4-hydroxyphenyl)propane was at most 10, and did not differ from that of the solution prepared by dissolving granulated solid 2,2-bis(4-hydroxyphenyl) propane in aqueous sodium hydroxide.

Comparative Example I-1

A 300-ml reactor equipped with a condenser and a stirrer was purged with nitrogen gas. 224 g of an aqueous sodium hydroxide solution having a concentration of 5.6% by weight, and 0.035 g of hydrosulfite serving as a reducing agent were put into the reactor. The mixture in the reactor was kept at 15° C.

Next, with stirring the mixture in the reactor at 350 rpm, 35 g of a melt (at 170° C.) of 2,2-bis(4-hydroxyphenyl) propane was poured into it. Having been poured thereinto, the melt of 2,2-bis(4-hydroxyphenyl)propane immediately solidified and gave large masses. At least 1 hour was taken to dissolve the masses.

Comparative Example I-2

A 300-ml reactor equipped with a condenser and a stirrer was purged with nitrogen gas. 224 g of an aqueous sodium hydroxide solution having a concentration of 5.6% by weight, and 0.035 g of hydrosulfite serving as a reducing agent were put into the reactor, and heated up to 85° C.

Next, with stirring the mixture in the reactor at 350 rpm, 35 g of a melt (at 170° C.) of 2,2-bis(4-hydroxyphenyl) propane was poured into it. Having been poured thereinto, the melt of 2,2-bis(4-hydroxyphenyl)propane immediately dissolved in the aqueous sodium hydroxide solution, without forming deposit.

However, the APHA color hue of the aqueous sodium hydroxide solution of 2,2-bis(4-hydroxyphenyl)propane fell between 20 and 25. This means the decomposition of 2,2-bis(4-hydroxyphenyl)propane.

EXAMPLE I-4

(1) Production of Polycarbonate Oligomer

The aqueous sodium hydroxide solution of 2,2-bis(4-hydroxyphenyl)propane obtained in Example I-1(the 2,2-bis (4-hydoxyphenyl)propane concentration in the solution= 13.5% by weight) was cooled to room temperature.

Next, the aqueous sodium hydroxide solution of 2,2-bis (4-hydroxyphenyl)propane at a flow rate of 138 liters/hr and a solvent, methylene chloride at a flow rate of 69 liters/hr were introduced into a tubular reactor having an inner diameter of 10 mm and a length of 10 m, through an orifice plate, with phosgene being introduced thereinto at a flow rate of 10.7 kg/hr, and these were continuously reacted for 3 hours. The tubular reactor used herein had a double-walled structure. With cooling water being circulated through the jacket of the reactor, the temperature inside the reactor was so controlled that the reaction mixture could be at 25° c. at the outlet.

The thus-obtained reaction mixture was kept static, and the aqueous phase separated was removed to obtain 220 liters of a methylene chloride phase. 170 liters of methylene chloride was added to the methylene chloride phase, and stirred to obtain a methylene chloride solution of polycarbonate oligomer. This had a polycarbonate oligomer concentration of 314.7 g/liter, a degree of polymerization of from 3 to 4, and a chloroformate group concentration of 0.74 N.

(2) Production of Polycarbonate Resin 3.28 liters of methylene chloride was added to 5.72 liters of the methylene chloride solution of polycarbonate oligomer obtained in the above step (1). The resulting methylene chloride solution of polycarbonate oligomer had a polycarbonate oligomer concentration of 200 g/liter and a chloroformate group concentration of 0.47 N, and this was put into a 20-liter reactor equipped with a stirrer. Next, 3,570 g of the aqueous sodium hydroxide solution of 2,2-bis(4-hydroxyphenyl)propane obtained in Example I-1 and kept at room temperature was added to this. In addition, 0.856 g of trimethylamine serving as a catalyst, and 47.5 g of p-tert-butylphenol serving as a terminator were added thereto.

With that, the mixture in the reactor was kept stirred at 600 rpm for 10 minutes in turbulent flow. Next, 167 ml of an aqueous sodium hydroxide solution having a concentration of 48% by weight was added to this, and further stirred at 200 rpm for 60 minutes in laminar flow.

After having been thus reacted, the reaction mixture was mixed with 5 liters of water and 5 liters of methylene chloride added thereto. Then, this was kept static for phase separation into an aqueous phase and a methylene chloride phase. The aqueous phase was removed, and the methylene chloride phase was washed with an aqueous 0.01 N sodium hydroxide solution and then with 0.1 N hydrochloric acid. Further washed with water to remove methylene chloride, this gave a flaky polycarbonate resin. The polycarbonate resin thus obtained had a viscosity-average molecular weight of 19,000.

II. Second Aspect of the Invention

In this section, the second aspect of the invention will be simply referred to as the invention.

In the method of the invention for producing a starting material for polycarbonate resin, a bisphenol compound prepared in melt in a process of bisphenol compound production is, without being solidified, directly mixed with water to be in liquid at a temperature not higher than the melting point of the bisphenol compound, and then dissolved in an aqueous alkali solution; and in the method of the invention for producing polycarbonate resin, the resulting aqueous alkali solution of the bisphenol compound is used as the starting material for polycarbonate resin production through interfacial polymerization.

In the method of the invention, the step of polycarbonate resin production through interfacial polymerization is per-se known, as so mentioned in the section of the first aspect of the invention.

For the details of the bisphenol compound that serves as the essential starting material in the polycarbonate resin production, and its production, referred to are the same as those described in the section of the first aspect of the invention.

In the invention, the molten bisphenol prepared in the manner as above is, without being solidified and granulated in a granulation step, directly mixed with water to be in liquid at a temperature not higher than the melting point of the bisphenol compound, and then dissolved in an aqueous alkali solution. For example, 2,2-bis(4-hydroxyphenyl) propane is mixed with water to be in liquid at a temperature falling between 98° C. and 155° C. The resulting aqueous alkali solution of the bisphenol compound is directly used for polycarbonate resin production, not requiring an additional step of dissolving the bisphenol compound in an aqueous alkali solution.

Without being solidified, the molten bisphenol compound is mixed with water to be in liquid even at a temperature not higher than the melting point of the bisphenol compound. Regarding the proportion of water to be mixed with the molten bisphenol compound to give a liquid mixture, for example, when 2,2-bis(4-hydroxyphenyl)propane is mixed with water and when the resulting liquid mixture is kept at 98° C., the ratio of water to the liquid mixture must be from 18% by weight to 85% by weight. If the temperature of the liquid mixture is elevated higher, the amount of water to be added to the bisphenol compound could be reduced more. The method of mixing the molten bisphenol with water is not specifically defined, for which, for example, any ordinary dissolution tank equipped with a line mixer or a stirrer may be employed. Preferably, the molten bisphenol and water are introduced into the apparatus in an inert gas atmosphere of nitrogen gas or the like in order to prevent the bisphenol compound from being in contact with oxygen.

The molten bisphenol compound is, without being solidified, directly mixed with. water to be in liquid at a temperature not higher than the melting point of the bisphenol compound, and then dissolved in an aqueous alkali solution. In this step, preferably, the temperature of the aqueous alkali solution is controlled to fall between 20 and 80° C. This is because, if the temperature of the aqueous alkali solution is lower than 20° C., the solubility of the bisphenol compound in the aqueous alkali solution lowers and a lot of time will be taken to dissolve the bisphenol compound in the solution. On the other hand, if the temperature is higher than 80° C., the bisphenol compound will be thermally decomposed and discolored, and, in addition, the aqueous alkali solution will corrode the apparatus.

For mixing the liquid mixture of the bisphenol compound and water with such an aqueous alkali solution, for example, employed is a dissolution tank equipped with a line mixer or a stirrer. Preferably, the atmosphere in the apparatus is previously purged with an inert gas such as nitrogen gas or the like so that the mixing operation can be effected in such an inert gas atmosphere.

For the aqueous alkali solution in which the liquid mixture of the molten bisphenol and water is dissolved, preferred is sodium hydroxide. In place of sodium hydroxide, however, any other alkali metal hydroxides and alkaline earth metal hydroxides may also be employed. The concentration of the aqueous alkali solution preferably falls between 2 and 47% by weight. Also preferably, the amount of the aqueous alkali solution to be used falls between 1.9 and 2.5 mols relative to one mol of the bisphenol to be dissolved in the solution. Regarding the reaction between bisphenol and alkali such as sodium hydroxide, one mol of bisphenol theoretically reacts with 2 mols of sodium hydroxide. In practical reaction, however, it is desirable that the amount of sodium hydroxide is excessive in some degree over bisphenol.

When the bisphenol compound is mixed with such an aqueous alkali solution, a reducing agent is preferably added thereto. The reducing agent may be any ordinary one. For example, preferred are sodium sulfite, sodium thiosulfate, sodium dithionite (hydrosulfite), etc. Its amount may fall between 10 and 1,000 ppm of the water content of the aqueous alkali solution. The reducing agent may be added to water which is to be mixed with a molten bisphenol compound, or may be added to an aqueous alkali solution, or may be added to water which is used for controlling the alkali concentration of the solution, or may be added to the aqueous alkali solution simultaneously with molten bisphenol compound added thereto. The reducing agent added improves the color tone of the polycarbonate resin that starts from the aqueous alkali solution of bisphenol compound obtained herein.

For the details of the polycarbonate resin production that starts from the thus-obtained, aqueous alkali solution of bisphenol compound, referred to are the same as those mentioned in the section of the first aspect of the invention.

The invention is described more concretely with reference to the following Examples and Comparative Examples, which, however, are not intended to restrict the scope of the invention.

EXAMPLE II-1

A melt (at 170° C.) of 2,2-bis(4-hydroxyphenyl)propane and water heated at 100° C. were fed into a line mixer via different pumps, and mixed. The flow rate of 2,2-bis(4-hydroxyphenyl)propane was 35 g/min; and that of water was 10 g/min. The residence time in the line mixer was 10 seconds. The apparatus was so cooled that the temperature of the mixture of 2,2-bis(4-hydroxyphenyl)propane and water could be 100° C. at the outlet of the line mixer.

The liquid mixture of 2,2-bis(4-hydroxyphenyl)propane and water that had been mixed in the line mixer and was fluid therein was then mixed with an aqueous sodium hydroxide solution (concentration, 5.9% by weight) at 80° C. in a different line mixer. The alkali solution contained 300 ppm of hydrosulfite. The flow rate of the liquid mixture of 2,2-bis(4-hydroxyphenyl)propane and water was 45 g/min; and that of the aqueous sodium hydroxide solution was 214 g/min. The residence time in the line mixer was 10 seconds.

In the solution of 2,2-bis(4-hydroxyphenyl)propane mixed and dissolved in the aqueous sodium hydroxide solution in the line mixer, no crystal of 2,2-bis(4-hydroxyphenyl)propane was found. The APHA color hue of the solution was at most 10. The solution was analyzed, and no decomposition product of 2,2-bis(4-hydroxyphenyl) propane was detected therein.

EXAMPLE II-2

The process of Example II-1 was repeated. In this, however, the temperature of the aqueous sodium hydroxide solution was 30° C. and the liquid mixture of 2,2-bis(4- hydroxyphenyl)propane and water was mixed with the aqueous sodium hydroxide solution for 30 seconds in the line mixer.

In the solution of 2,2-bis(4-hydroxyphenyl)propane dissolved in the aqueous sodium hydroxide solution, no crystal of 2,2-bis (4-hydroxyphenyl) propane was found. The APHA color hue of the solution was at most 10. The solution was analyzed, and no decomposition product of 2,2-bis(4-hydroxyphenyl)propane was detected therein.

Comparative Example II-1

Not mixed with water heated at 100° C., a melt (at 170° C.) of 2,2-bis(4-hydroxyphenyl)propane was tried to mix with an aqueous sodium hydroxide solution at 15° C. (its alkali concentration was 5.6% by weight, and it contained 300 ppm of hydrosulfite) in a line mixer.

In this process, however, the melt of 2,2-bis(4-hydroxyphenyl)propane solidified in the line mixer and did not mix with the solution.

Comparative Example II-2

Not mixed with water heated at 100° C., a melt (at 170° C. ) of 2,2-bis(4-hydroxyphenyl)propane was fed into a line mixer along with an aqueous sodium hydroxide solution at 85° C. (its alkali concentration was 5.6% by weight, and it contained 300 ppm of hydrosulfite), and the two were mixed therein.

In the solution of 2,2-bis(4-hydroxyphenyl)propane dissolved in the aqueous sodium hydroxide solution, no crystal of 2,2-bis(4-hydroxyphenyl)propane was found. However, the APHA color hue of the solution fell between 15 and 20. The solution was analyzed, and isopropenylphenol resulting from decomposition of 2,2-bis(4-hydroxyphenyl) propane was detected therein.

EXAMPLE II-3

(1) Production of Polycarbonate Oligomer

The aqueous sodium hydroxide solution of 2,2-bis(4-hydroxyphenyl)propane obtained in Example II-1 (the 2,2-bis(4-hydoxyphenyl)propane concentration in the solution= 13.5% by weight) was cooled to room temperature.

Next, the aqueous sodium hydroxide solution of 2,2-bis (4-hydroxyphenyl)propane at a flow rate of 138 liters/hr and a solvent, methylene chloride at a flow rate of 69 liters/hr were introduced into a tubular reactor having an inner diameter of 10 mm and a length of 10 m, through an orifice plate, with phosgene being introduced thereinto at a flow rate of 10.7 kg/hr, and these were continuously reacted for 3 hours. The tubular reactor used herein had a double-walled structure. With the temperature inside the reactor was so controlled that the reaction mixture could be at 25° C. at the outlet.

The thus-obtained reaction mixture was kept static, and the aqueous phase separated was removed to obtain 220 liters of a methylene chloride phase. 170 liters of methylenechloride was added to the methylene chloride phase, and stirred to obtain a methylene chloride solution of polycarbonate oligomer. This had a polycarbonate oligomer concentration of 314.7 g/liter, a degree of polymerization of from 3 to 4, and a chloroformate group concentration of 0.74 N.

(2) Production of Polycarbonate Resin 3.28 liters of methylene chloride was added to 5.72 liters of the methylene chloride solution of polycarbonate oligomer obtained in the above step (1). The resulting methylene chloride solution of polycarbonate oligomer had a polycarbonate oligomer concentration of 200 g/liter and a chloroformate group concentration of 0.47 N, and this was put into a 20-liter reactor equipped with a stirrer. Next, 3,570 g of the aqueous sodium hydroxide solution of 2,2-bis(4-hydroxyphenyl)propane obtained in Example II-1 and kept at room temperature was added to this. In addition, 0.856 g of trimethylamine serving as a catalyst, and 47.5 g of p-tert-butylphenol serving as a terminator were added thereto.

With that, the mixture in the reactor was kept stirred at 600 rpm for 10 minutes in turbulent flow. Next, 167 ml of an aqueous sodium hydroxide solution having a concentration of 48% by weight was added to this, and further stirred at 200 rpm for 60 minutes in laminar flow.

After having been thus reacted, the reaction mixture was mixed with 5 liters of water and 5 liters of methylene chloride added thereto. Then, this was kept static for phase separation into an aqueous phase and a methylene chloride phase. The aqueous phase was removed, and the methylene chloride phase was washed with an aqueous 0.01 N sodium hydroxide solution and then with 0.1 N hydrochloric acid. Further washed with water to remove methylene chloride, this gave a flaky polycarbonate resin. The polycarbonate resin thus obtained had a viscosity-average molecular weight of 19,000.

Industrial Applicability

According to the invention, a step of granulating a bisphenol compound can be omitted in the process of preparing the starting material for polycarbonate resin, and a step of dissolving the bisphenol compound can be omitted in the process of producing polycarbonate. Therefore, the equipment cost and the operation cost for the steps can be saved, and the production costs for the resin can be reduced.

What is claimed is:

1. A method for producing a starting material for polycarbonate resin production, comprising:
preparing a melt of a bisphenol compound in a process of bisphenol compound production; and
mixing and dissolving the molten bisphenol compound in an aqueous alkali solution at 20 to 80° C., thereby preparing a bisphenol starting material for the production of a polycarbonate resin by interfacial polymerization.

2. The method according to claim 1, wherein the bisphenol compound is a bis(4-hydroxyphenyl)alkane.

3. The method according to claim 1, wherein the bisphenol compound is a 4,4'-dihydroxybiphenyl, a bis(4-hydroxyphenyl)methane, a bis(2-hydroxyphenyl)methane, a bis(4-hydroxyphenyl)ethane, a bis(2-hydroxyphenyl)ethane, a bis(4-hydroxyphenyl)propane, a bis(4-hydroxyphenyl) butane, a bis(hydroxyphenyl)alkane, a bis(4-hydroxyphenyl)ether, a bis(4-hydroxyphenyl)sulfide, a bis (4-hydroxyphenyl)sulfoxide, a bis(4-hydroxyphenyl) sulfone, a bis(4-hydroxyphenyl)ketone, a bis (hydroxyphenyl)fluorene, a dihydroxy-p-terphenyl, a bis (hydroxyphenyl)pyrazine, a bis(hydroxyphenyl)menthane, a bis[2-(4-hydroxyphenyl)-2-propyl]benzene, a dihdroxynaphthalene or a dihydroxybenzene.

4. The method according to claim 1, wherein the alkali solution is a solution of an alkali metal hydroxide or an alkaline earth metal hydroxide.

5. The method according to claim 4, wherein the alkali solution contains a reducing agent in an amount of 10 to 1,000 ppm by weight of the aqueous alkali solution.

6. A method for producing a polycarbonate resin, comprising:
preparing a melt of a bisphenol compound in a process of bisphenol compound production;

mixing and dissolving the molten bisphenol compound in an aqueous alkali solution at 20 to 80° C.; and the conducting interfacial polymerization employing the prepared bisphenol containing aqueous solution as a reactant, thereby preparing a polycarbonate resin product.

7. The method according to claim 6, which comprises reacting the solution of bisphenol compound with phosgene.

8. A method for producing a starting material for polycarbonate resin production, comprising:

preparing a melt of a bisphenol compound in a process of bisphenol compound production; and without solidification of the melt, mixing the molten bisphenol compound into liquid water at a temperature higher than the melting point of the bisphenol compound; and then dissolving the water solution obtained in an aqueous alkali solution.

9. The method according to claim 8, wherein the bisphenol compound is a bis(4-hydroxyphenyl)alkane.

10. The method according to claim 8, wherein the bisphenol compound is a 4,4'-dihydroxybiphenyl, a bis(4-hydroxyphenyl)methane, a bis(2-hydroxyphenyl)methane, a bis(4-hydroxyphenyl)ethane, a bis(2-hydroxyphenyl)ethane, a bis(4-hydroxyphenyl)propane, a bis(4-hydroxyphenyl)butane, a bis(hydroxyphenyl)alkane, a bis(4-hydroxyphenyl)ether, a bis(4-hydroxyphenyl)sulfide, a bis(4-hydroxyphenyl)sulfoxide, a bis(4-hydroxyphenyl)sulfone, a bis(4-hydroxyphenyl)ketone, a bis(hydroxyphenyl)fluorene, a dihydroxy-p-terphenyl, a bis(hydroxyphenyl)pyrazine, a bis(hydroxyphenyl)menthane, a bis[2-(4-hydroxyphenyl)-2-propyl]benzene, a dihydroxynaphthalene or a dihydroxybenzene.

11. The method according to claim 8, wherein the liquid water is at a temperature ranging from 98 to 155° C.

12. The method according to claim 8, wherein, when the bisphenol is 2,2-bis(4-hydroxyphenyl)propane and mixed with the liquid water at the temperature of 98° C., the ratio of water to the mixture ranges from 18 to 85% by weight.

13. The method according to claim 8, wherein, when the alkali solution is a solution of an alkali metal hydroxide or an alkaline earth metal hydroxide.

14. The method according to claim 8, wherein the temperature of the aqueous alkali solution ranges from 20 to 80° C.

15. The method according to claim 8, wherein the alkali solution contains a reducing agent in an amount of 10 to 1,000 ppm by weight of the aqueous alkali solution.

16. A method for producing a polycarbonate resin, comprising:

preparing a melt of a bisphenol compound in a process of bisphenol compound production;

without solidification of the melt, mixing the molten bisphenol compound into liquid water at a temperature higher than the melting point of the bisphenol compound;

dissolving the water solution obtained in an aqueous alkali solution; and then conducting interfacial polymerization employing the prepared bisphenol containing aqueous alkali solution as a reactant, thereby preparing a polycarbonate resin product.

17. The method according to claim 16, which comprises reacting the solution of bisphenol compound with phosgene.

* * * * *